(12) United States Patent
Lin et al.

(10) Patent No.: US 7,250,509 B1
(45) Date of Patent: Jul. 31, 2007

(54) METHOD FOR PREPARING MELAMINE SALT OF PENTAERYPOLYOL PHOSPHORIC ACID

(75) Inventors: Yu-Sheng Lin, Longtan Township, Taoyuan County (TW); Wen-Chiung Su, Longtan Township, Taoyuan County (TW); Chong Ma, Longtan Township, Taoyuan County (TW); Yuen-Hsin Peng, Longtan Township, Taoyuan County (TW)

(73) Assignee: Chung Shan Institute of Science and Technology, Taoyuan County (TW)

( * ) Notice: Subject to any disclaimer, the term of this patent is extended or adjusted under 35 U.S.C. 154(b) by 3 days.

(21) Appl. No.: 11/443,293

(22) Filed: May 31, 2006

(51) Int. Cl.
   *C07D 251/54* (2006.01)
   *C07F 9/6571* (2006.01)
(52) U.S. Cl. ........................ 544/195; 558/74
(58) Field of Classification Search ................ 544/195; 558/74
   See application file for complete search history.

(56) References Cited

U.S. PATENT DOCUMENTS

| 4,454,064 A | 6/1984 | Halpern et al. |
| 4,478,998 A | 10/1984 | Halpern et al. |
| 6,737,526 B1 * | 5/2004 | Ma et al. ................ 544/195 |
| 6,833,467 B2 | 12/2004 | Ma et al. |

FOREIGN PATENT DOCUMENTS

| TW | 591032 | 6/2004 |
| TW | I221474 | 10/2004 |

* cited by examiner

*Primary Examiner*—Venkataraman Balasubramanian
(74) *Attorney, Agent, or Firm*—Rabin & Berdo, P.C.

(57) ABSTRACT

A method for preparing a melamine salt of pentaerypolyol phosphoric acid is provided. The method comprises the following steps of: ball milling a mixture of pentaerypolyol and phosphorus pentoxide ($P_2O_5$) under a solvent-free reacting environment to obtain a pentaerypolyol phosphoric acid, and ball milling a mixture of a pentaerypolyol phosphoric acid and melamine without organic solvent reacting environment to obtain a melamine salt of pentaerypolyol phosphoric acid.

15 Claims, 2 Drawing Sheets

METHOD FOR PREPARING MELAMINE SALT OF PENTAERYPOLYOL PHOSPHORIC ACID

BACKGROUND

1. Field of Invention

This invention relates to a method for preparing a flame retardant material and in particular to a method for preparing a melamine salt of pentaerypolyol phosphoric acid.

2. Related Art

Conventional processes for manufacturing flame retardant materials or flame retardant additive materials, applied for electric wire, connect wire, wiring board or hot melt glue, such as a polyolefin flame retardant material containing phosphorous, oxygen and carbon, are all involving chemical processes using a large amount of organic solvents as reaction medium and catalysts.

For example, in U.S. Pat. No. 6,833,467 to Ma issued Dec. 21, 2004 and in U.S. Pat. No. 6,737,526 to Ma issued May 18, 2004, a large amount of toluene solvent, together with pentaerythritol and phosphorus pentoxide reactants, was used to run the two step esterification followed by the next step of neutralization with melamine to form melamine salt of bis-(pentaerythritol phosphate) phosphoric acid and melamine salt of pentaerythritol phosphoric acid. Also used in the two-step esterification process is a metal halide catalyst.

The main concept of the above inventions is to introduce a ball milling mechanochemical manufacturing process. However, since a large amount of organic solvents is used in that reaction, the environment requirements are hard to satisfy. In order to satisfy the environment requirements, the costs for pollution control must increase and will thus lead to an economically unsuccessful production. Besides, the use of a catalyst will also increase impurities of the products.

U.S. Pat. No. 4,454,064 discloses a method for preparing pentaerythritol phosphate regarding a reaction between pentaerythritol and phosphorus oxychloride reactants in a dioxane solvent under a temperature of 75 to 125° C. This is a useful intermediate in the preparation of flame-retardant materials, polyurethanes, and plasticizers.

U.S. Pat. No. 4,478,998 discloses a method for preparing an amino-s-triazine salt containing phosphoric acid, which is represented by the following formula,

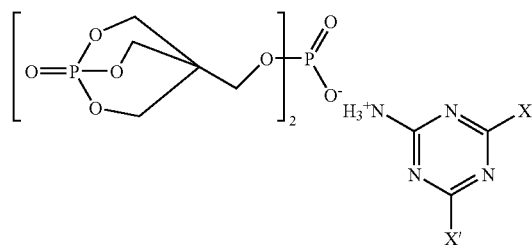

in which the X and X' are ammonium groups, therefore the salt will be a melamine salt of bis-(pentaerythritol phosphate) phosphoric acid. The salt can be used as a flame retardant additive for some specific polymer compositions.

However, the preparing methods as mentioned above all involve the usage of a large amount of solvents and will generate hydrochloric acid vapor, for which a large amount of water is required to wash away HCl from the product mixture, and solution containing excess POCl$_3$ (phosphorus oxychloride) during the reaction, which will hardly ever satisfy the environment requirement and will increase the cost when taking the expenses for the environment requirement in mind.

SUMMARY

One object of the invention is to provide a method for preparing a melamine salt of pentaerypolyol phosphoric acid without using solvent (ex. toluene or xylene) and catalyst, which makes the process much easier, cost effective and environmentally friendly without decreasing the yield, and can thus eliminate the problems of recycling the solvent and the derivative environmental problems. Therefore, this invention provides an environmentally friendly manufacturing process with increasing purity of products and reducing cost.

According to the invention, an embodiment of a method for preparing a melamine salt of pentaerypolyol phosphoric acid includes the steps of: ball milling a mixture of pentaerypolyol and phosphorus pentoxide ($P_2O_5$) under a solvent-free reacting environment to obtain pentaerypolyol phosphoric acid; followed by ball milling a mixture of the pentaerypolyol phosphoric acid and melamine without organic solvent reacting environment to obtain a melamine salt of pentaerypolyol phosphoric acid.

The pentaerypolyol can be neopentyl glycol (NPG), 1,1,1-tris(hydroxymethyl)ethane (tHME), pentaerythritol (PE) or dipentaerythritol (DPE).

This embodiment can further include a preheating step before the step of ball milling the mixture of the pentaerypolyol and the phosphorus pentoxide ($P_2O_5$) for increasing the reaction rate.

In summary, the features of the invention include: using a mechanochemical synthesis method, such as using a ball mill as a reactor to run the ball milling process; using a non-solvent process; and using no catalysts in the esterification step.

BRIEF DESCRIPTION OF THE DRAWINGS

The present invention will become more fully understood from the detailed description given below, which is for illustration only and thus is not limitative of the present invention, wherein.

DETAILED DESCRIPTION

Figure 1:
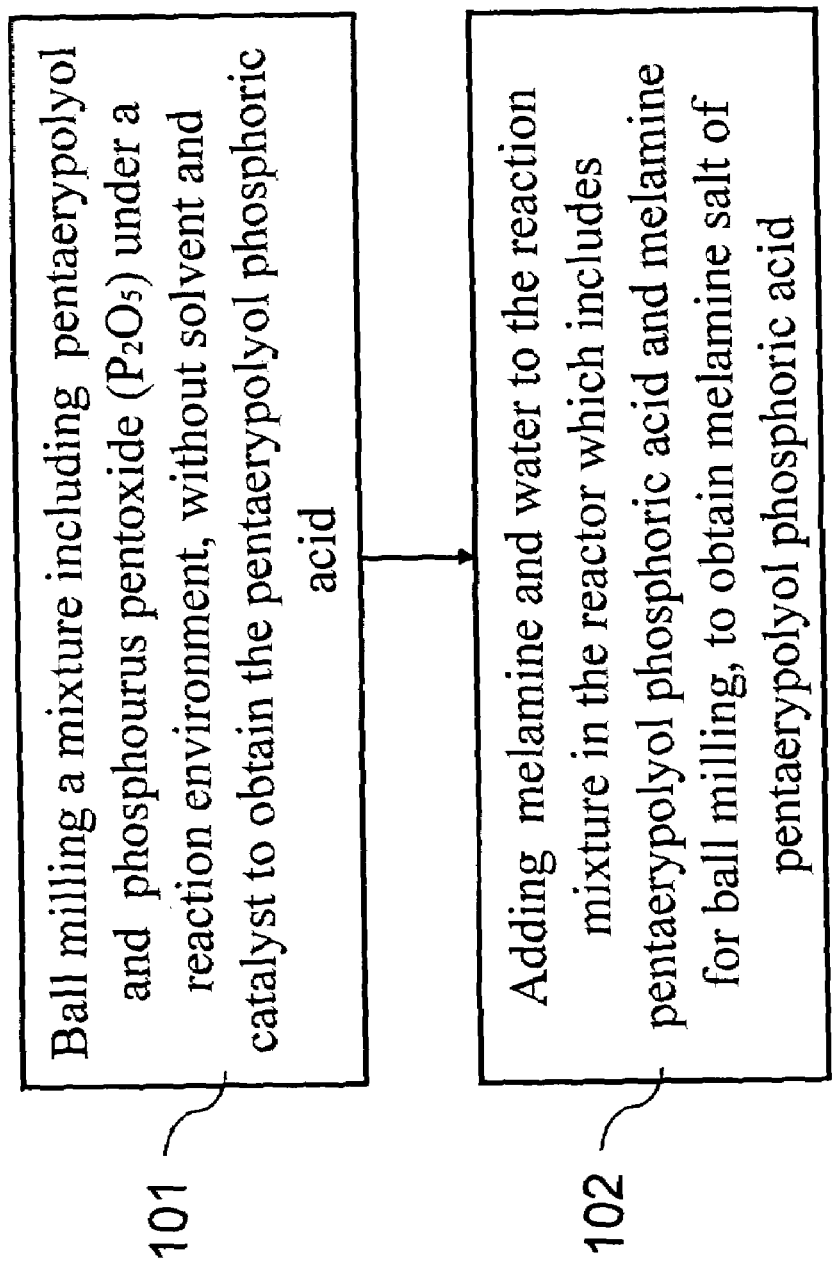
FIG. 1 shows the flow chart of an embodiment of a method according to the invention.

The conventional method for preparing a melamine salt of pentaerypolyol phosphoric acid includes two major steps: the esterification step for pentaerypolyol and phosphourus pentoxide; and the neutralization step for pentaerypolyol phosphoric acid and melamine. For example, when the reactants are pentaerythritol and phosphourus pentoxide, the reaction can be properly represented by the following formula.

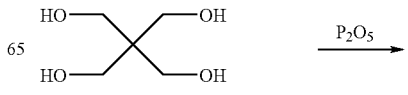

-continued

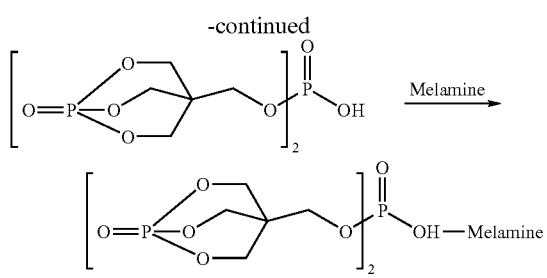

After the esterification step, the pentaerypolyol phosphoric acid produced can be neutralized with melamine to form the melamine salt of pentaerythritol phosphoric acid.

In a synergistic flame-retarding reaction involving phosphorous, nitrogen and carbon sources, the melamine decomposes within a thermal decomposition temperature range of the melt pentaerypolyol phosphoric acid, to produce non-poisonous and incombustibility vapors for foaming and inflating the decomposed pentaerypolyol phosphoric acid and making it an inflated carbonized layer, to gain a thermal isolation property.

However, a problem occurs during the manufacturing process using phosphorus pentoxide ($P_2O_5$) as reactant. The activity of the $P_2O_5$ is so strong that it can react with almost all kinds of solvents, limiting the choice of the solvent to only toluene or xylene, In these solvents, however, the pentaerythritol phosphoric acid becomes a molten sticky mass under high temperature (about above 85° C.). As a result, the molten sticky mass will be hard to separate, stir, mix and add reactants. Also, although solvents like toluene or xylene will not react with the phosphourus pentoxide, they are toxic which will cause a safety concern to the working environment. So one concept of the invention is to use a ball mill as a reactor in order to react and grind simultaneously for achieving the total reaction and dispersion purposes. In the mean time a solvent is not necessary.

The reactor can be, for example, a one-liter ball mill with balls of two-centimeter diameter made of ceramic or zirconium oxide.

Although the solvent would not react with $P_2O_5$, and help the reactant PE to convert into a melted state, however, under such reaction condition, the reactant PE is easy to stick together to become an un-easy separated mass or chunk during the reaction so as to cause the problem of uneven mixing, hard stirring, and difficulty in adding reactants for the reaction. On the other hand, this kind of solvent is poisonous and harmful for the operation environment.

More detailed, the concept of the invention is using a mechanochemical synthesis process, where, instead of stirring by conventional mechanical stirring method, a ball mill is used as a reactor in which the collisions occurred between the phosphourus pentoxide and the pentaerypolyol by ball milling will accomplish the purpose of total reaction and dispersion. In the mean time, heat is generated during collision process to promote the formation of the melamine salt of pentaerypolyol phosphoric acid without any organic solvents and/or catalysts. When necessary, water can be the solvent. As a result, this process is easier and not harmful to the environment.

Please refer to FIG. 1, one preferred embodiment of the method according to the invention includes the steps of: ball milling a mixture including pentaerypolyol and phosphourus pentoxide ($P_2O_5$) by making use of a one-liter ball mill and balls of two-centimeter diameter enough for the milling process under a reaction environment without solvent and catalyst to obtain the pentaerypolyol phosphoric acid (step 101); and adding melamine and water to the reaction mixture in the reactor, which includes pentaerypolyol phosphoric acid and melamine, for ball milling to obtain melamine salt of pentaerypolyol phosphoric acid (step 102).

Figure 2:
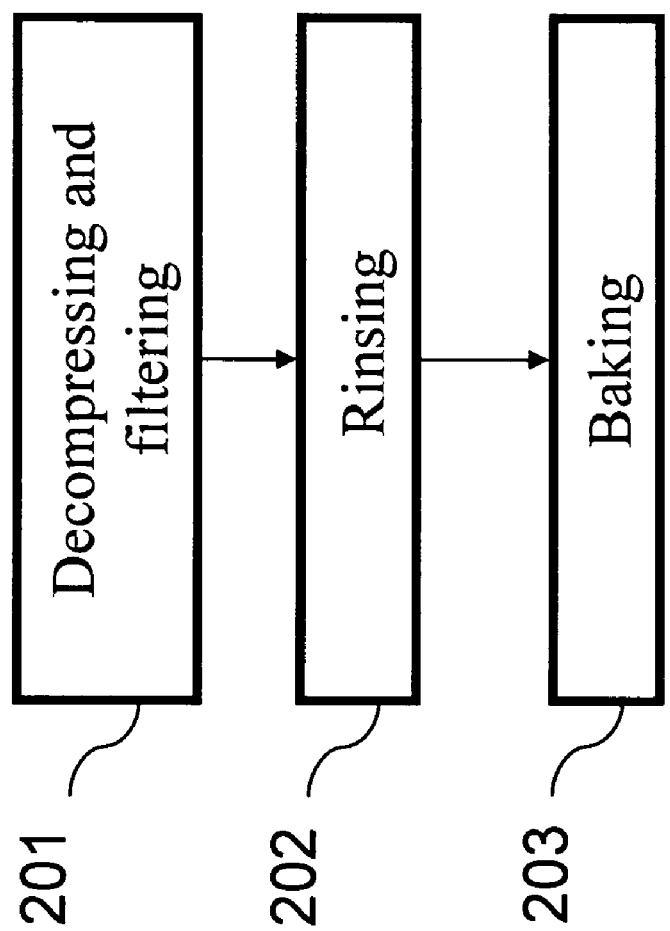
FIG. 2 shows the process steps proceeding for the products obtained by the method according to the invention.

Please refer to FIG. 2, the process can further include some product processing steps such as a decompressing step and a filtering step (step 201), a rinsing step (step 202), and a baking step by using an oven (step 203).

In this process, the one-liter ball mill can be the reactor and ceramic balls or zirconium oxide balls of two-centimeter diameter can be used.

The reactant, pentaerypolyol, is an i-pentane based polyol compound. Therefore the polyol compound can be neopentyl glycol (hereinafter refer to NPG) 2, 1,1,1-tris(hydroxymethyl)ethane (hereinafter refer to tHME) 3, pentaerythritol (hereinafter refer to PE) 4 or dipentaerythritol (hereinafter refer to DPE) 5, depending on the number of the hydroxyl group it includes. The structures of these compounds are shown below.

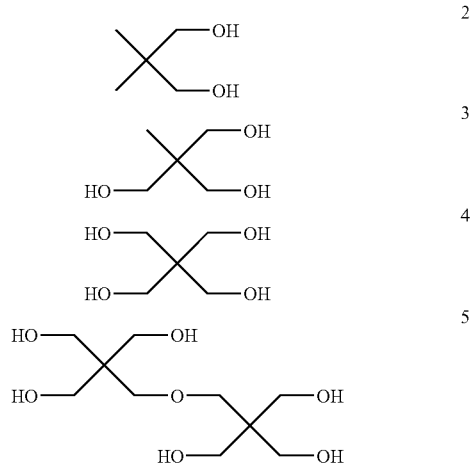

In the embodiments of this specification, products obtained are named after the abbreviation (ex. NPG mentioned above) plus "BM" (the abbreviation of Ball Mill). Therefore, the labeling of the products which comes from the 2, 3, 4, 5 reactants will be NPGBM, tHMEBM, PEBM and DPEBM respectively.

Thereinafter, the reactants 2, 3, 4 and 5 above will be used as reactants in the processes respectively for describing the invention.

Working Example 1

Process of Preparing a NPGBM

A one-liter ball mill as a reactor and ceramic balls with diameter of 2 cm were used. The ball mill bowl and balls can be preheated to 80 to 150° C., preferably to 110° C. for half an hour. Then, add 12.2 gram NPG and 25 gram $P_2O_5$ to the ball mill in a proper order. Seal it and then start mechanical grinding. Sample it after one-hour reaction. Dissolve the sample in dimethyl sulfoxide (hereinafter refer to DMSO) to run $^{31}$P-MNR to identify the main components in the products obtained for determining the reaction extent. Next, add 400 milliliters of water and 25.5 gram of melamine into the ball mill for reacting 90 minutes. After that, decompress and filter it and then rinse and bake it at 110° C. for 3 hours in an oven. The product obtained is 62.8 gram.

Under the same reaction condition above but without preheating the ball mill, a product of 68.38 gram is obtained.

Another embodiment is provided for preparing the NPG-BMA. A one-liter ball mill as a reactor and ceramic balls with diameter of 2 cm were used. The ball mill bowl and balls can be preheated to 80 to 150° C., preferably to 110° C. for half an hour. Then, add 15 gram MPG and 14.3 gram $P_2O_5$ to the ball mill in a proper order. Seal it and then start mechanical grinding. Sample it after one hour reaction by running $^{31}$P-NMR for determining the reaction extent. Next, add 400 milliliters of $CH_3CN$ and 25.5 gram of melamine into the ball mill for reacting 90 minutes. After that, decompress and filter it, then rinse it, and finally bake it at 110° C. for 3 hours in an oven. The product obtained weighs 56.2 gram. The yield is 99.9%.

Under the same reaction condition as above but without the preheating step, a product of 54 gram is obtained. The yield is also 99%.

Working Example 2

Process of Preparing a tHMEBM

A one-liter ball mill as a reactor and ceramic balls with diameter of 2 cm were used. The ball mill bowl and balls can be preheated to 80 to 150° C., preferably to 110° C. for half an hour. Then, add 15 gram tHME and 18.6 gram $P_2O_5$ to the ball mill in a proper order. Seal it and then start mechanical grinding. Sample it after one-hour reaction by running $^{31}$P-NMR for determining the reaction extent. Next, add 500 milliliters of water and 33.1 gram of melamine into the ball mill to grind for 90 minutes. After that, decompress and filter it and then rinse it with acetone, and bake it at 110° C. for 3 hours in an oven. The product obtained weighs 61 gram. The yield is 92%.

Working Example 3

Process of Preparing a PEBM

A one-liter ball mill as a reactor and two-centimeter diameter ceramic balls are chosen. The ball mill bowl and balls can be preheated to 80 to 150° C., preferably to 90 to 100° C. Then, add 13.6 gram PE and 8.5 gram $P_2O_5$ to the ball mill in a proper order. Put the ceramic ball into the ball mill and seal it and then start mechanical grinding for 1 hours. Add water and melamine into the ball mill to grind for 60 minutes. The reaction product includes 79.2% of the main product and 20.8% of phosphoric acid. The yield is greater than 95%.

Another embodiment is provided for preparing the PEBM. A one liter ball mill as a reactor and two-centimeter diameter ceramic balls are used. The ball mill bowl and balls can be preheated to 80 to 150° C., preferably to 110° C. for half an hour. Then, add 16 gram PE and 32 gram $P_2O_5$ to the ball mill in a proper order. Seal it and then start mechanical grinding. Sample it after one hour reaction by running $^{31}$P-NMR for determining the reaction extent. The chemical shift of phosphoric acid is at 0ppm and the chemical shift of the intermediate is at −6 ppm. Next, add 500 milliliters of water and 63 gram of melamine into the ball mill to grind for 60 minutes. After that, decompress and filter it then rinse it, and finally bake it at 160° C. in an oven. The yield is 96%.

Working Example 4

Process of Preparing a DPEBM

A one liter ball mill as a reactor and two-centimeter diameter ceramic balls are chosen. The ball mill bowl and balls can be preheated to 80 to 150° C., preferably to 110° C. for half an hour. Then, add 20 gram DPE and 24 gram $P_2O_5$ to the ball mill in a proper order. Seal it and then start mechanical grinding. Sample it after one-hour reaction by running $^{31}$P-NMR for determining the reaction extent. Next, add 500 milliliters of water and 48 gram of melamine into the ball mill to grind for 60 minutes. After that, decompress and filter it and then rinse it with acetone and bake it at 110° C. in an oven for 3 hours. The product obtained is 84.3 gram. The yield is 92%.

In summary, it is realized that using a ball mill as a reactor to perform the mechanochemical synthesis of pentaerypolyol phosphoric acid by reacting proper amounts of pentaerythritol and $P_2O_5$ in a time about 2 hours without any solvent and under room temperature is really workable. If it is preheated, for example to a preferred temperature of 90 to 120° C., the esterificatioin can be accelerated so that the reaction time can be further reduced to 1 hour.

If the pentaerythritol is grinded in toluene by a ball mill to reduce its particle size before reaction, the reaction rate and the purity of the product can be further improved.

Comparing the process claimed in this invention to the conventional process, this invention has the following advantages: no hydrochloride vapor produced; no contaminated waste water containing HCl produced from the neutralization; no process necessary for adding excess phosphorus oxychloride; the reduction of reacting time; better yield and purity of the product, and avoidance of using organic solvent and catalyst.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments, which do not depart from the spirit and scope of the invention.

What is claimed is:

1. A catalyst-free method for preparing a melamine salt of pentaerypolyol phosphoric acid, comprising the steps of:
   a. ball milling a first mixture comprised of pentaerypolyol and phosphorus pentoxide ($P_2O_5$), which includes no catalyst, in a reacting environment which is free of solvent to obtain a pentaerypolyol phosphoric acid, wherein ball milling takes place in a ball mill used as a reactor; and
   b. ball milling a second mixture comprised of said pentaerypolyol phosphoric acid and melamine, which includes no catalyst, in a reacting environment which is free of organic solvent, to obtain the melamine salt of pentaerypolyol phosphoric acid.

2. The catalyst-free method of claim 1, wherein ball milling in step (a) proceeds at a temperature ranging from room temperature to 150° C.

3. The catalyst-free method of claim 1, wherein the ball mill is preheated to a temperature of 110° C. for one half hour.

4. The catalyst-free method of claim 1, wherein the pentaerypolyol is selected from the group consisting of 2,2-dimethyl-1,3-neopentyl glycol, 1,1,1-tris(hydroxymethyl)-ethane (tHME), pentaerythritol (PE) and dipentaerythritol (DPE).

5. The catalyst-free method of claim 1, wherein the second mixture further comprises water.

6. The catalyst-free method of claim 1, wherein ball milling in step (a) proceeds for a time ranging up to 6 hours.

7. The catalyst-free method of claim 6, wherein ball milling in step (a) proceeds for a time ranging from 1 to 6 hours.

8. The catalyst-free method of claim 6, wherein ball milling in step (a) proceeds for a time of 1 hour.

9. A catalyst-free method for preparing a melamine salt of pentaerypolyol phosphoric acid, comprising:
   a. ball milling a first mixture comprised of pentaerypolyol and phosphorus pentoxide ($P_2O_5$), which includes no catalyst, in a reacting environment which is free of solvent for six hours to obtain a pentaerypolyol phosphoric acid, wherein ball milling takes place in a ball mill used as a reactor; and
   b. ball milling a second mixture comprised of said pentaerypolyol phosphoric acid and melamine which includes no catalyst, in a reacting environment which is free of organic solvent, to obtain the melamine salt of pentaerypolyol phosphoric acid.

10. The catalyst-free method of claim 9, wherein ball milling in step (a) proceeds at a temperature ranging from room temperature to 150° C.

11. The catalyst-free method of claim 9, wherein the ball mill is preheated to a temperature of 110° C. for one half hour.

12. The catalyst-free method of claim 9, wherein the pentaerypolyol is selected from the group consisting of 2,2-dimethyl-1,3-neopentyl glycol, 1,1,1-tris(hydroxymethyl)-ethane (tHME), pentaerythritol (PE) and dipentaerythritol (DPE).

13. The catalyst-free method of claim 9, wherein the second mixture further comprises water.

14. The catalyst-free method according to claim 1, wherein the ball mill is preheated before the step of ball milling to a temperature ranging from 80 to 150° C.

15. The catalyst-free method according to claim 9, wherein the ball mill is preheated before the step of ball milling to a temperature ranging from 80 to 150° C.

* * * * *